(12) United States Patent  
Bennett

(10) Patent No.: US 8,814,904 B2
(45) Date of Patent: Aug. 26, 2014

(54) SURGICAL SUTURE SYSTEM

(75) Inventor: William F. Bennett, Sarasota, FL (US)

(73) Assignee: Ziptek LLC., Sarasota, FL (US)

(*) Notice: Subject to any disclaimer, the term of this patent is extended or adjusted under 35 U.S.C. 154(b) by 657 days.

(21) Appl. No.: 12/912,313

(22) Filed: Oct. 26, 2010

(65) Prior Publication Data

US 2012/0101524 A1 Apr. 26, 2012

(51) Int. Cl.
*A61B 17/04* (2006.01)
*A61B 17/06* (2006.01)

(52) U.S. Cl.
CPC ... *A61B 17/0401* (2013.01); *A61B 2017/06176* (2013.01); *A61B 2017/045* (2013.01); *A61B 2017/0427* (2013.01); *A61B 2017/0456* (2013.01); *A61B 2017/0438* (2013.01); *A61B 2017/0462* (2013.01); *A61B 2017/0441* (2013.01); *A61B 2017/0404* (2013.01); *A61B 17/0466* (2013.01); *A61B 2017/044* (2013.01); *A61B 17/06166* (2013.01)
USPC .......................................... 606/232; 606/300

(58) Field of Classification Search
USPC ................. 606/228–232, 300, 301, 304, 305; 24/129 R, 127, 128, 130, 129 B
See application file for complete search history.

(56) References Cited

U.S. PATENT DOCUMENTS

| 4,898,156 | A | | 2/1990 | Gatturna et al. | |
|---|---|---|---|---|---|
| 5,370,661 | A | | 12/1994 | Branch | |
| 5,413,585 | A | | 5/1995 | Pagedas | |
| 5,584,835 | A | * | 12/1996 | Greenfield | 606/232 |
| 5,938,686 | A | | 8/1999 | Benderev et al. | |
| 5,948,000 | A | * | 9/1999 | Larsen et al. | 606/232 |
| 6,013,083 | A | | 1/2000 | Bennett | |
| 6,015,410 | A | | 1/2000 | Tormala et al. | |
| 6,117,162 | A | | 9/2000 | Schmieding et al. | |
| 6,206,886 | B1 | | 3/2001 | Bennett | |
| 6,293,961 | B2 | | 9/2001 | Schwartz et al. | |
| 6,491,714 | B1 | * | 12/2002 | Bennett | 606/232 |
| 6,533,802 | B2 | | 3/2003 | Bojarski et al. | |
| 7,303,577 | B1 | | 12/2007 | Dean | |
| 7,530,990 | B2 | | 5/2009 | Perriello et al. | |
| 7,585,311 | B2 | | 9/2009 | Green et al. | |
| 7,615,061 | B2 | | 11/2009 | White et al. | |
| 7,637,926 | B2 | | 12/2009 | Foerster et al. | |
| 7,658,750 | B2 | | 2/2010 | Li | |
| 7,658,751 | B2 | | 2/2010 | Stone et al. | |
| 7,674,274 | B2 | * | 3/2010 | Foerster et al. | 606/232 |

(Continued)

FOREIGN PATENT DOCUMENTS

WO WO 2012/058301 5/2012

OTHER PUBLICATIONS

U.S. Appl. No. 13/281,963, filed Oct. 26, 2011, Bennett.
U.S. Appl. No. 13/664,717, filed Oct. 31, 2012, Bennett.

*Primary Examiner* — Julian W Woo
(74) *Attorney, Agent, or Firm* — Frijouf, Rust & Pyle, P.A

(57) ABSTRACT

A surgical suture system for tissue repair and reattachment of torn tissue to a tissue substrate, medical prosthesis or medical implant. The system includes an elongated flexible suture member having a plurality of longitudinally spaced protuberances along a length thereof and a plurality of tissue engaging members each including two spaced apart locking apertures sized to receive the suture member passed therethrough to allow longitudinal movement of the suture member in only one direction through the locking apertures for suture member tightening.

6 Claims, 15 Drawing Sheets

(56) References Cited

U.S. PATENT DOCUMENTS

| | | |
|---|---|---|
| 7,682,374 B2 | 3/2010 | Foerster et al. |
| 7,686,838 B2 | 3/2010 | Wolf et al. |
| 7,695,494 B2 | 4/2010 | Foerster |
| 7,713,285 B1 * | 5/2010 | Stone et al. .................. 606/232 |
| 2002/0004668 A1 | 1/2002 | Bartlett |
| 2002/0004669 A1 | 1/2002 | Bartlett |
| 2002/0007196 A1 | 1/2002 | Bartlett |
| 2006/0058844 A1 * | 3/2006 | White et al. .................. 606/232 |
| 2006/0106422 A1 | 5/2006 | Del Rio et al. |
| 2006/0106423 A1 | 5/2006 | Weisel et al. |
| 2007/0156151 A1 | 7/2007 | Guan et al. |
| 2007/0282375 A1 | 12/2007 | Hindrichs et al. |
| 2008/0082113 A1 | 4/2008 | Bishop et al. |
| 2008/0234731 A1 * | 9/2008 | Leung et al. .................. 606/232 |
| 2009/0248071 A1 * | 10/2009 | Saint et al. .................. 606/232 |
| 2009/0287227 A1 * | 11/2009 | Newell et al. .................. 606/148 |
| 2010/0160963 A1 * | 6/2010 | Fallin et al. .................. 606/232 |
| 2012/0101526 A1 | 4/2012 | Bennett |

\* cited by examiner

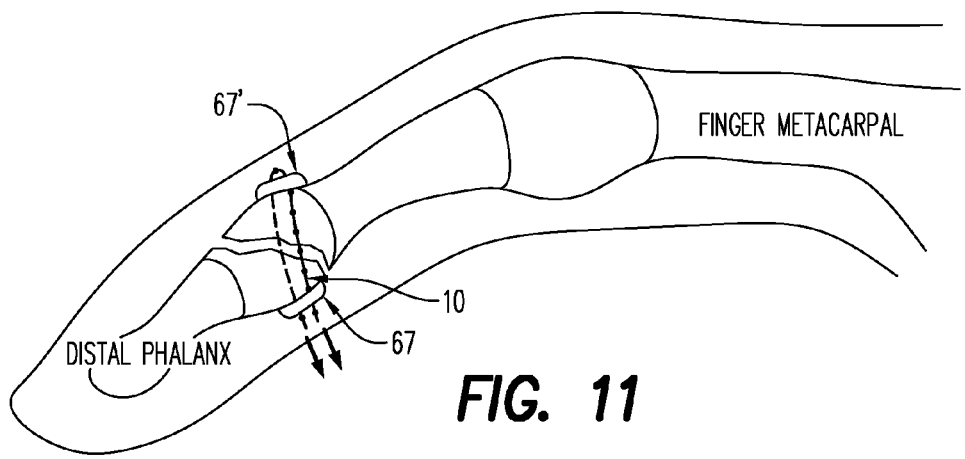
FIG. 11
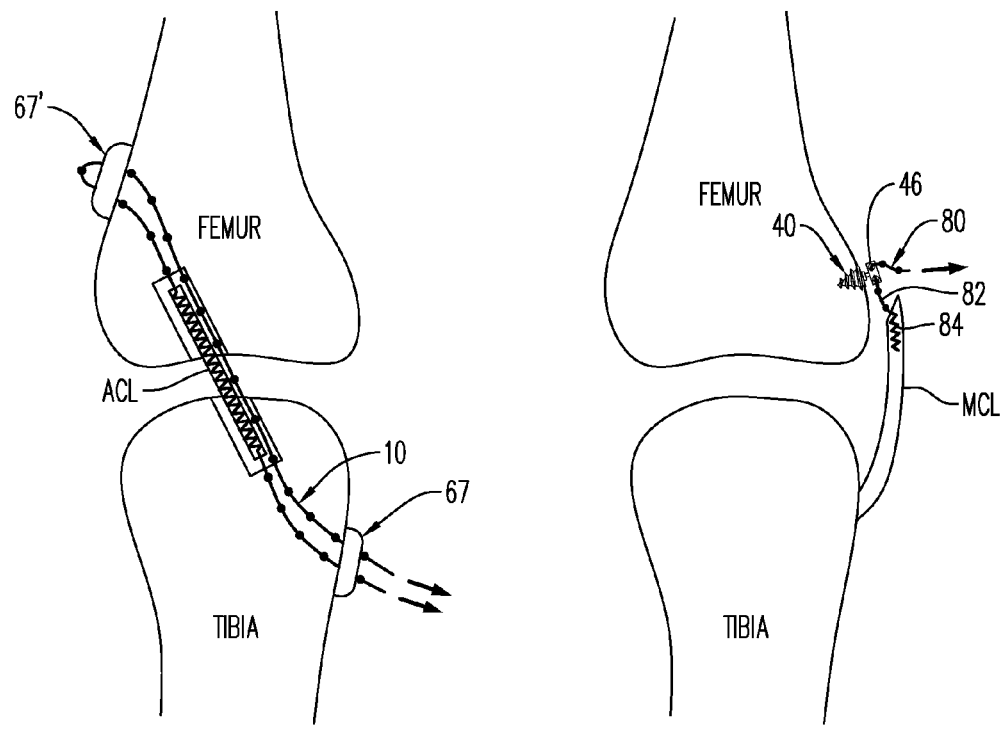
FIG. 12
FIG. 13

HIP LABRAL REPAIR

DISTAL BICEPS REPAIR

ANKLE SYNDESMOTIC DISRUPTION

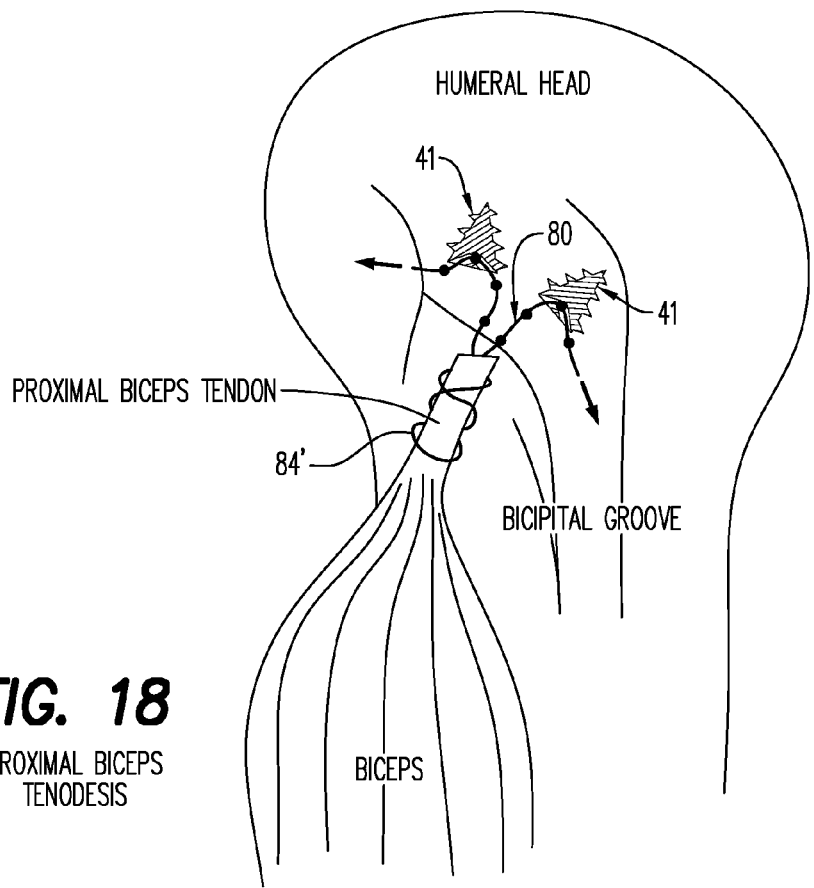
FIG. 18
PROXIMAL BICEPS TENODESIS
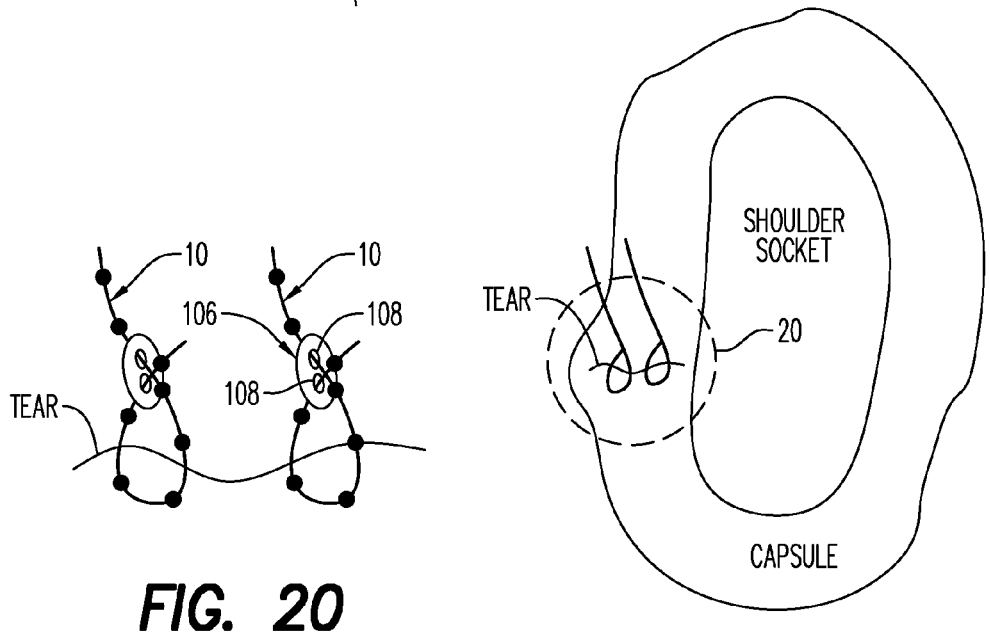
FIG. 20
FIG. 19
JOINT CAPSULE REPAIR WITH FREE CAPTURE WITHOUT ANCHOR

SHOULDER LABRAL REPAIR

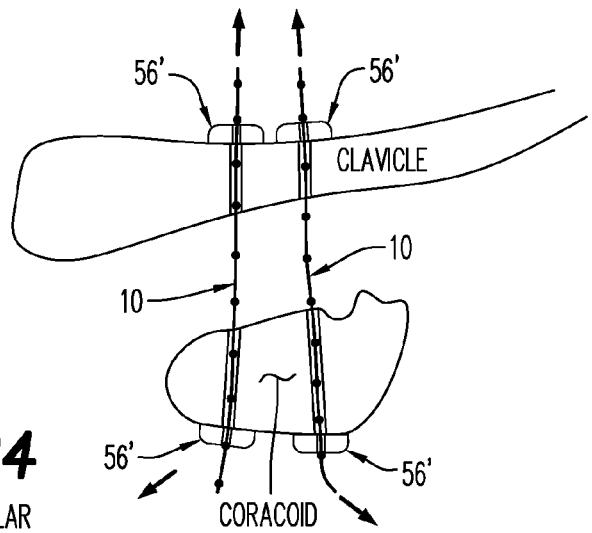
FIG. 24
CORACOCLAVICULAR
LIGAMENT REPAIR
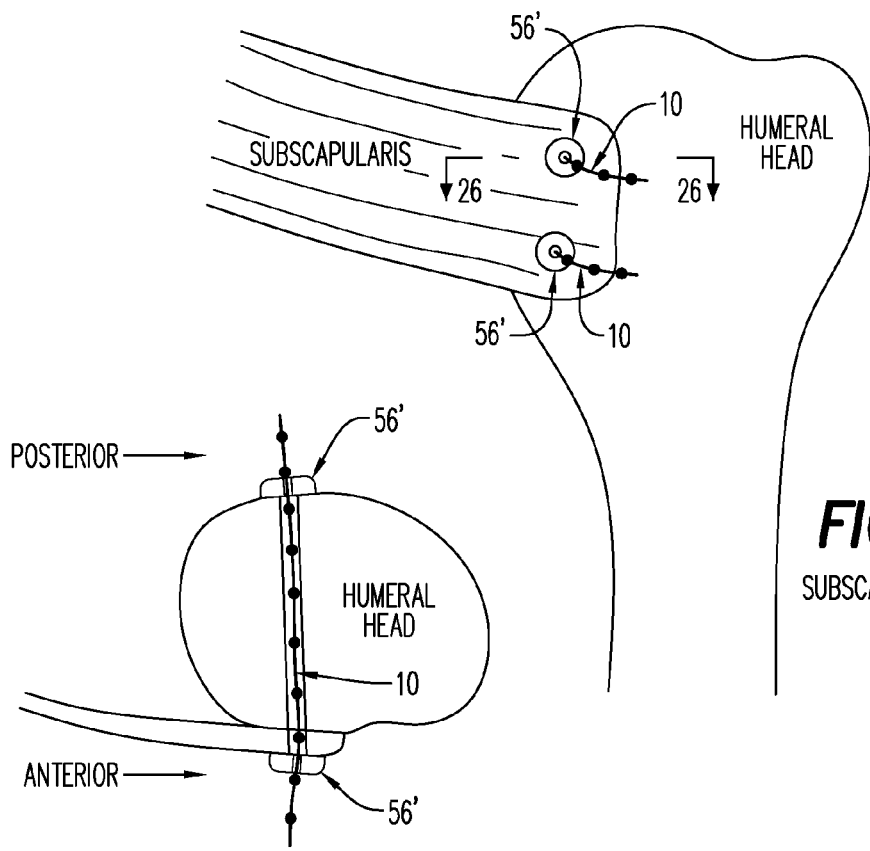
FIG. 25
SUBSCAPULARIS REPAIR
FIG. 26

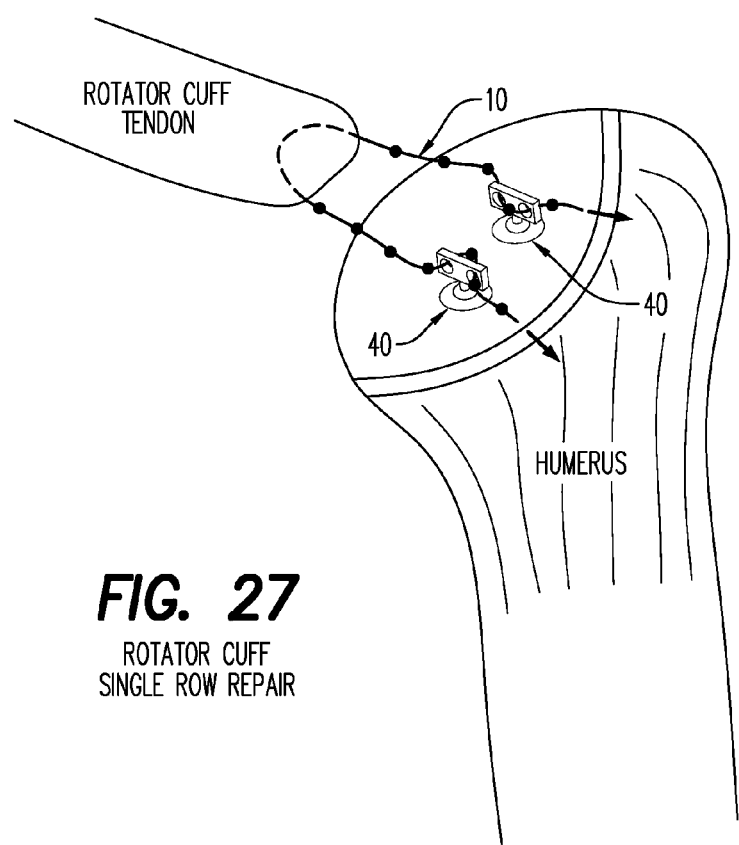
FIG. 27
ROTATOR CUFF
SINGLE ROW REPAIR
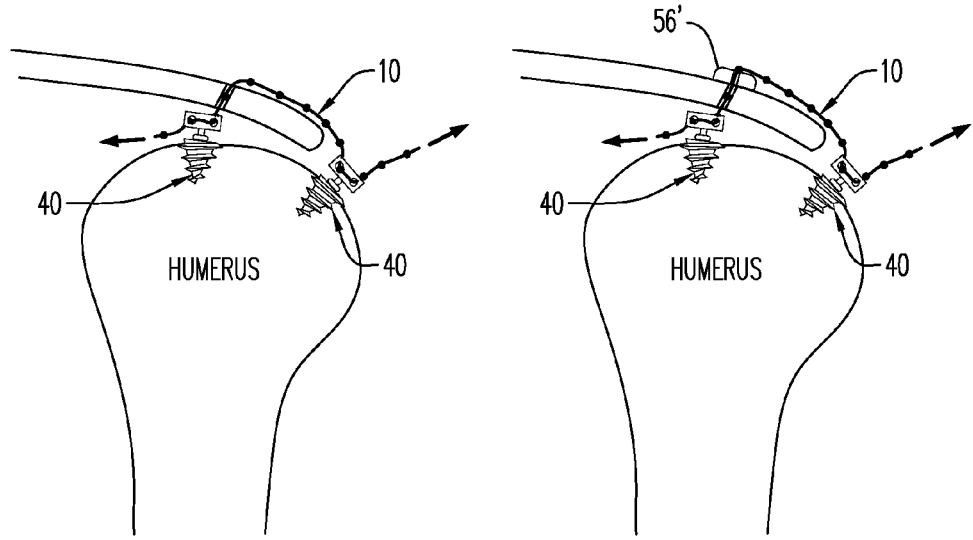
FIG. 28   FIG. 29
DOUBLE ROW
REPAIR

MENISCAL REPAIR
SAGITTAL VIEW

MENISCAL REPAIR
FIXED OR WITH
INTERFACE

MENISCAL REPAIR
MULTIPLE REPAIRS

SURGICAL SUTURE SYSTEM

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to surgical apparatus and methods for repair of torn tissue, and more particularly to an apparatus and method for arthroscopic and other surgical repair of torn tissue and tissue reattachment by providing a system for suturing and anchoring the torn tissue, together, against other tissue substrates, or for attaching tissue to medical implants.

2. Description of Related Art

The rotator cuff is composed of four tendons that blend together to help stabilize and move the shoulder. When a tear occurs in the rotator cuff of the shoulder, it is often necessary to reattach the torn tendon or tendons to the bone of the humeral head. In a common prior art rotator cuff reattachment technique, the torn cuff is punctured by a punch, and prethreaded suture anchor screws (soft tissue fasteners) are drilled into the head of the humerus bone and the sutures threaded through the anchor screws are passed through the cuff in a difficult procedure using suture relay devices to pass the sutures through the tissue. After the suture strands are passed through the tissue, they are knotted and tied together to secure the reattached rotator cuff to the humerus head. Other types of prior art suture anchors are conically shaped members that are pressed into holes drilled into the bone and engage the cancellous mass surrounding the drilled hole.

A major problem with the above described suture anchoring technique is that the threaded suture anchor screws or conically shaped anchors are threadedly or otherwise secured to the cancellous bone mass beneath the near cortex of the head of the humerus, and depend on this cancellous mass for fixation. It is well known that the cancellous bone mass is susceptible to osteopenic changes (diminished amount of bone tissue).

As a result, the pull-out strength of suture anchors which are dependent on the cancellous bone mass beneath the cortex of the bone is subject to becoming diminished with time, and the anchors will tend to loosen, thereby possibly requiring a second operation to remove the loosened suture anchor.

Another problem with the conventional technique is that, in most cases, the sutures are not passed through the tissue when the anchor is set, and thus a difficult procedural step is required using devices such as punches and suture relays to pass and tie the sutures through the torn tissue.

Additionally, many anchor/suture devices require knots to be tied which is difficult with minimally invasive surgery and having a "knotless" solution is an advantage.

In my prior U.S. Pat. No. 6,491,714, an apparatus and method for arthroscopic repair of torn tissue such as a rotator cuff was taught wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool.

The deployment tool is passed through the inner cannula and a hole is drilled until the expandable wings clear the far end of the hole, a sufficient distance to allow the wings to expand to a diameter larger than the diameter of the drilled hole. The deployment tool, inner cannula, drill guide and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

Unlike conventional soft tissues anchors which are anchored in the cancellous bone mass beneath the near cortex of the bone, the '714 teaching in one embodiment provides a suture anchor which is engaged on the exterior of the far cortex of the bone and completely bypasses the cancellous bone mass. The cortex of the bone is much less susceptible to osteopenia than the cancellous interior of the bone. The sutures are passed through the tissue when the anchor is set, and thus the difficult procedural step and use of devices such as punches and suture relays to pass and tie the sutures through the torn tissue is eliminated.

Calibrated markings on the '714 deployment system allow for precise measurement of the far cortex and precise measurement of the depth of insertion and engagement of the anchor device on the far cortex, such that structures beyond the cortex are not violated, and the button hold-down feature eliminates the traditionally difficult arthroscopic tying techniques.

In another broader aspect of the '714 invention, the surgical apparatus includes any form of a tissue substrate anchor of a conventional well-known structure, an elongated suture member securable at its proximal end to the anchor, and a separate torn tissue retainer which lockably engages as desired along the length of the suture member. The suture member extending through the torn tissue from the anchor and the tissue substrate. The torn tissue retainer is movable along the length of the exposed portion of the suture member until it is tightly positioned against the torn tissue and automatically locked in that position by non-reversible lockable engagement with the suture member. A separate tissue gripping member formed preferably as a semi-flexible plate or disc having a substantially larger surface area than the tissue retainer is also provided for enhanced retention of the torn tissue in place against the outer surface of the tissue substrate.

Still another broad aspect of this '714 invention is directed to a surgical apparatus which includes an integrally formed tissue substrate anchor having an elongated suture member formed as a unit therewith. A separate disc-shaped retainer lockingly engages with the exposed distal end of the suture portion at any desired point along the suture interlocking portion. The tissue retainer is therefore moveable along the length of the exposed engaging members of the suture member for tightening the tissue layer against the tissue substrate. Utilized another way, a tear such as that found within a torn meniscus may be reconnected utilizing this embodiment of the invention.

Currently, soft-tissue fixation products that utilize "knotless" technology and screws rely on an "interference-fit" for holding power between the screw and bone. In general, non-screw anchors have a pullout strength near 200 newtons, and screws can have upwards of 400 newtons of pullout strength.

The patent technology allows for the introduction of a revolutionary type of anchor for soft-tissue fixation to bone. Screws, as opposed to hook-type anchors, have the strongest pullout strength, "ZIP-TIE" patented technology will introduce its technology to the eyelet of screws. Specifically, it will attach one member of the suture to screws and this will allow for a ratcheting of the suture member through the suture capture or retainer or suture anchor, thereby creating a very strong construct.

The traditional repair of soft tissue requires sutures to be passed through the tissue. A knot is tied, which holds the torn tissue together, allowing for healing. Minimally invasive surgical techniques are being utilized through "button-hole" size incisions. Surgery is performed with instruments that pass through cannulas (like drainage culverts or pipes). Knots that would be utilized for this type of repair are tied and must be slid down through these cannulas. This technique can be difficult, result in adequate repair strength, provide for poor tissue approximation, for some surgeons, it may result in an inability to proceed with a minimally invasive approach secondary to the advanced technical difficulty, and finally, can add significant operative time to surgical procedures. USCO's patented technology is akin to a "cable or tie-wrap" that is utilized for holding electric wire or cables together. Based upon the patented interface, a "pipe-line" of products will be created using knot-less, self-locking interface as a technology development platform.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

The present disclosure is broadly directed to a surgical suture system for tissue repair and reattachment of torn tissue to a tissue substrate, medical prosthesis or medical implant. The system includes an elongated flexible suture member having a plurality of longitudinally spaced protuberances along a length thereof, and a plurality of tissue engaging members such as suture tissue restraints, anchors, and medical implants each including two spaced apart locking apertures sized to receive the suture member passed therethrough to allow longitudinal movement of the suture member in only one direction through the locking apertures for suture member tightening and retention.

It is therefore an object of this invention to provide a surgical suture system for tissue repair and reattachment of torn tissue together, to a tissue substrate or medical implant.

It is another object of this invention to provide a surgical suture system for repair of torn tissue such as a torn rotator cuff utilizing uniquely configured tissue engaging members, each of which include a double locking aperture arrangement of two closely spaced together locking apertures which receive the unique suture and cooperate for only one-way movement during tightening of the suture to bring torn tissue into a desired healing orientation.

A broad aspect of this disclosure provides for the reattachment of any torn or damaged tissue or artificial tissue to any form of tissue substrate or together by the use of a uniquely configured substrate anchor or tissue restraint having a double locking aperture arrangement for receiving a suture having spaced apart protuberances along the length of the suture. The suture tissue restraint or substrate anchor, or more broadly the tissue engaging member, is configured for movement of the suture itself through the pair of locking apertures in only one direction so that any tightening movement of the suture within the tissue engaging member is locked from reverse movement therebetween. A variety of spaced protuberance configurations along the length of the flexible elongated suture member are disclosed for this one-way locking movement engagement within one or more of the tissue engaging members each having the two spaced apart locking apertures formed therethrough to lockingly receive the suture members.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

Figure 10:
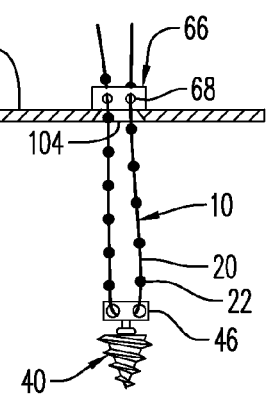

FIG. 10 is an elevation view of a typical installation arrangement of the elongated suture member 10 in locking engagement with a suture anchor 40 and a suture tissue restraint 66.

FIG. 11 is a simplified pictorial view of one aspect of the invention utilized to repair and restrain a broken distal phalanx of a finger metacarpal.

FIG. 12 is an elevation view utilizing another aspect of the present invention to repair torn ACL tissue of a knee joint.

FIG. 13 is an elevation view utilizing another aspect of the present invention to repair a torn MCL of a knee joint.

Figure 14:
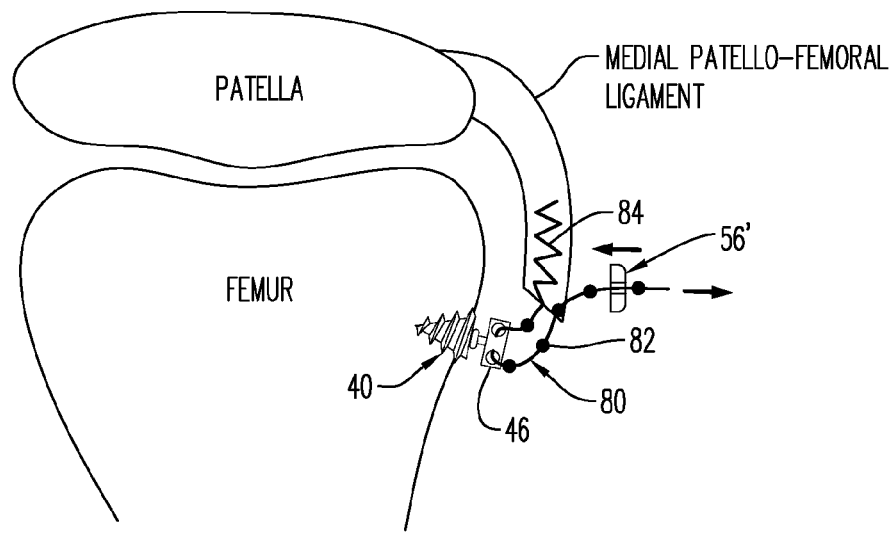

FIG. 14 is a side elevation view showing another aspect of the invention utilized to repair a torn medial patella-femoral ligament.

Figure 15:
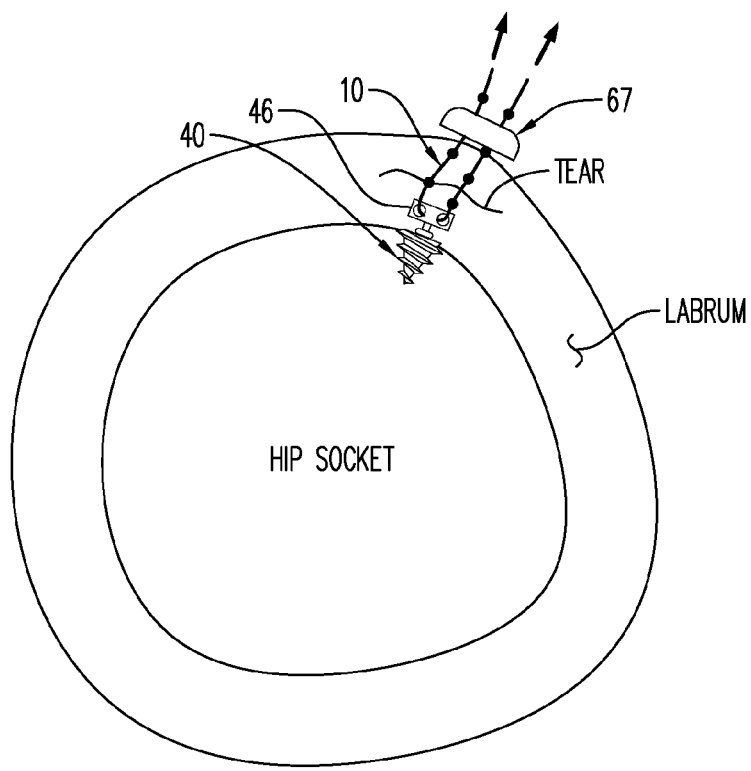

FIG. 15 is a simplified section view showing another aspect of the invention utilized to repair a tear in the hip labrum.

Figure 16:
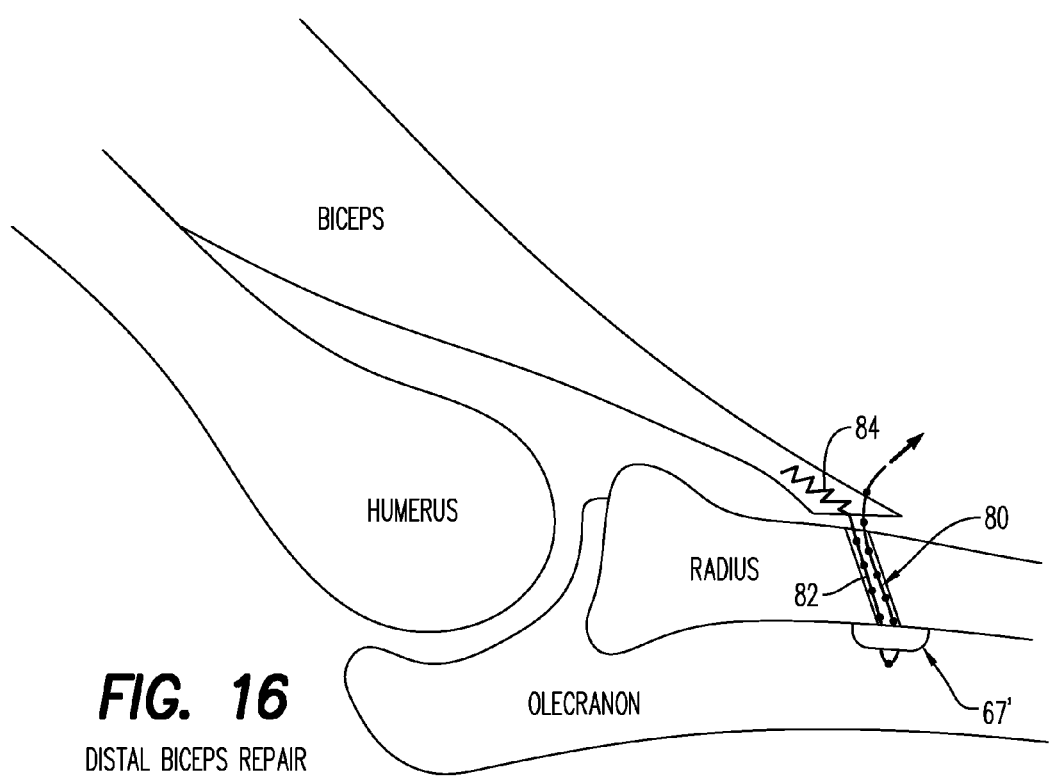

FIG. 16 depicts another aspect of the invention utilized to reattach the torn distal end of the biceps.

Figure 17:
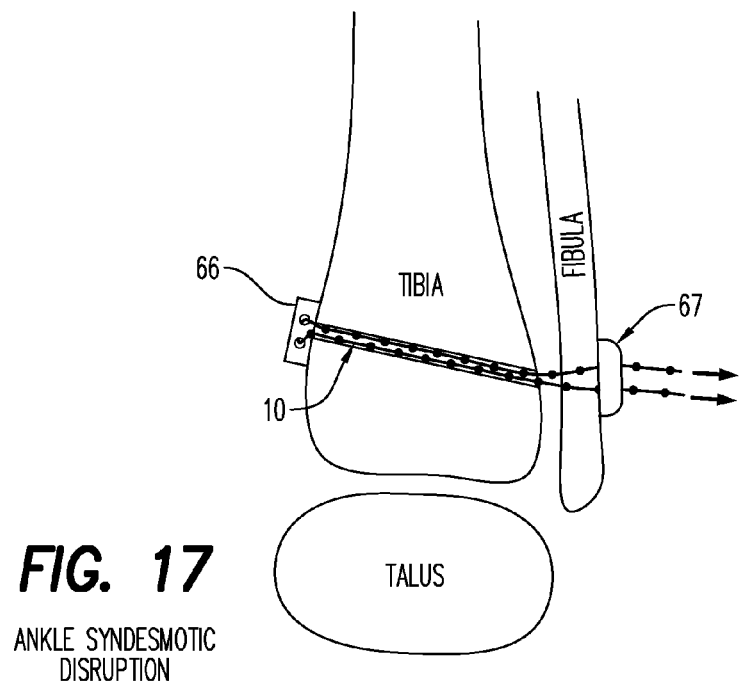

FIG. 17 shows a schematic view utilizing another aspect of the invention to reattach the fibula of an ankle syndesmotic disruption.

FIG. 18 is a side elevation view depicting another aspect of the invention for reattaching the proximal biceps tendon to the humeral head.

FIG. 19 is a simplified section view depicting another aspect of the invention for repairing a tear in the joint capsule which surrounds a shoulder socket.

FIG. 20 is an enlargement of area 20 in FIG. 19.

Figure 21:
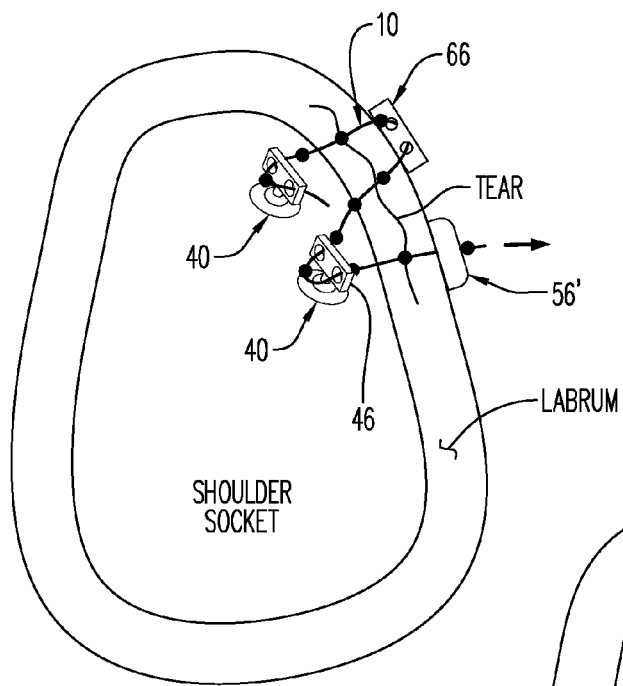
Figure 22:
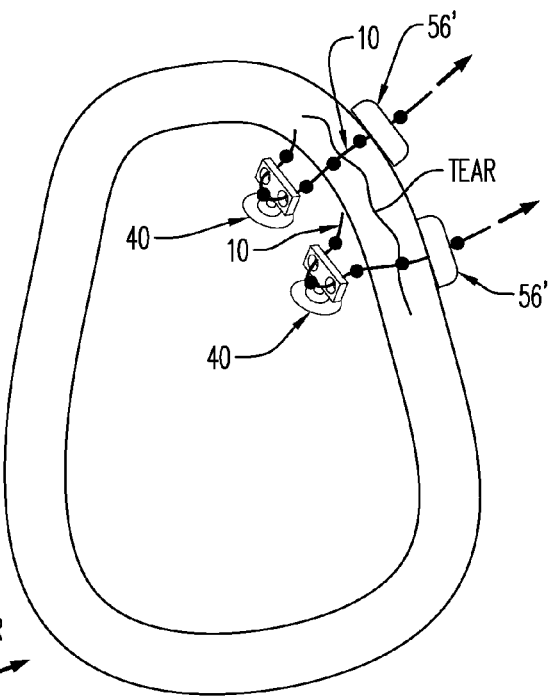
Figure 23:
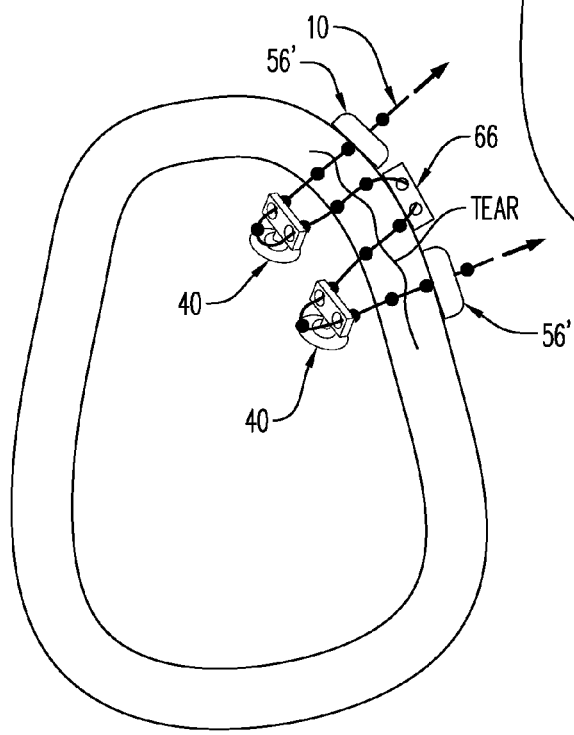

FIGS. 21 to 23 show other aspects of the invention utilized to repair a tear in the shoulder labrum surrounding a shoulder socket.

FIG. 24 is a simplified side elevation view showing another aspect of the invention utilized to effect a coracoclavicular ligament repair.

FIG. 25 is an elevation view utilizing another aspect of the invention to effect a subscapularis-to-humeral head repair.

FIG. 26 is a section view in the direction of arrows 26-26 in FIG. 25.

FIG. 27 is an elevation view showing another aspect of the invention utilized to reattach a rotator cuff tendon to the top of the humerus.

FIG. 28 and FIG. 29 depict alternate aspects of the invention utilized to effect the repair shown in FIG. 27.

Figure 30:
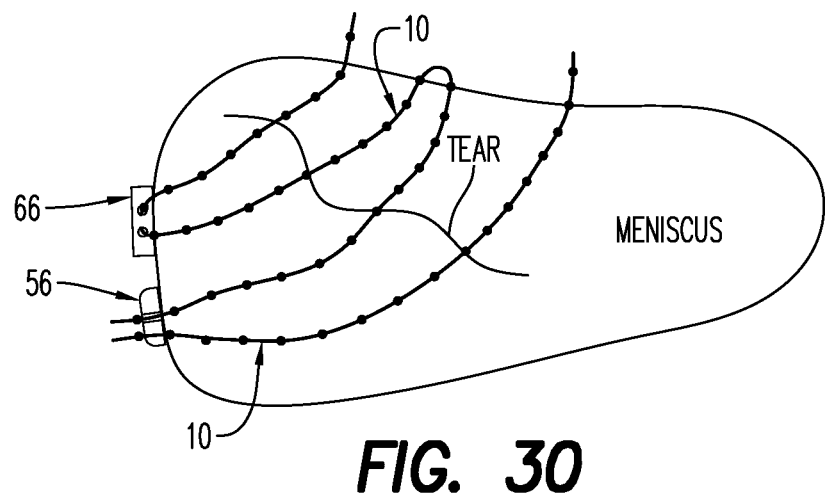
Figure 31:
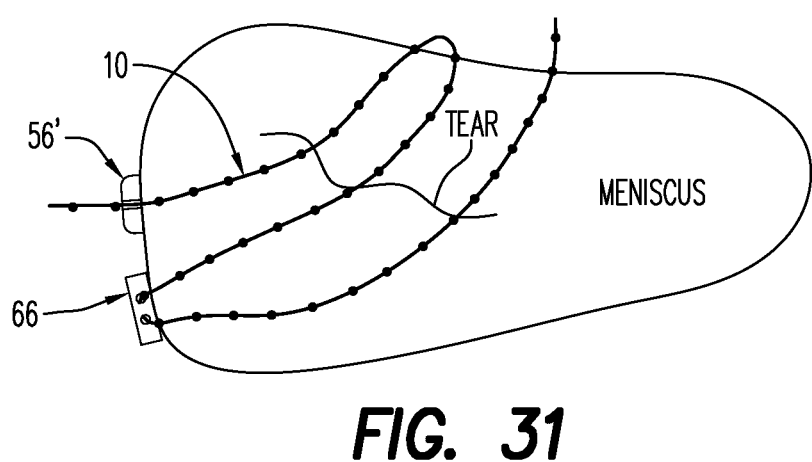

FIGS. 30 and 31 depict sagittal views depicting alternate aspects of the invention utilized to effect a meniscus tear repair.

Figure 32:
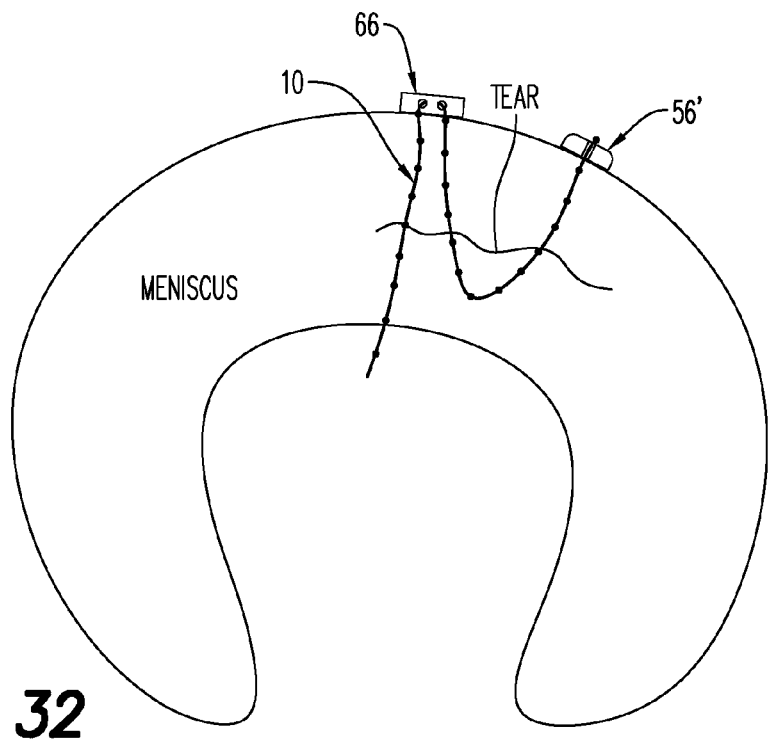
Figure 33:
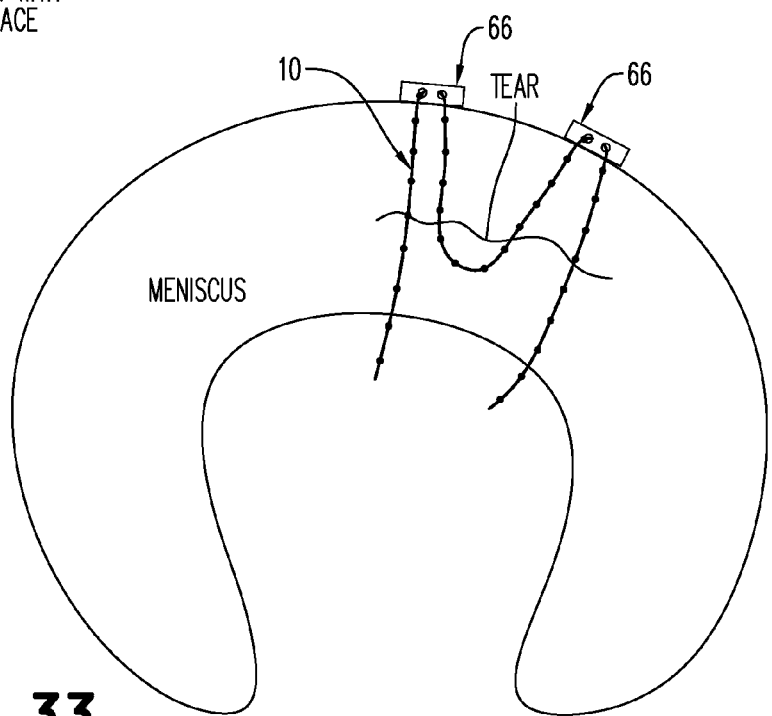

FIGS. 32 and 33 depict alternate aspects of the invention utilized to effect a torn meniscal repair.

Figure 34:
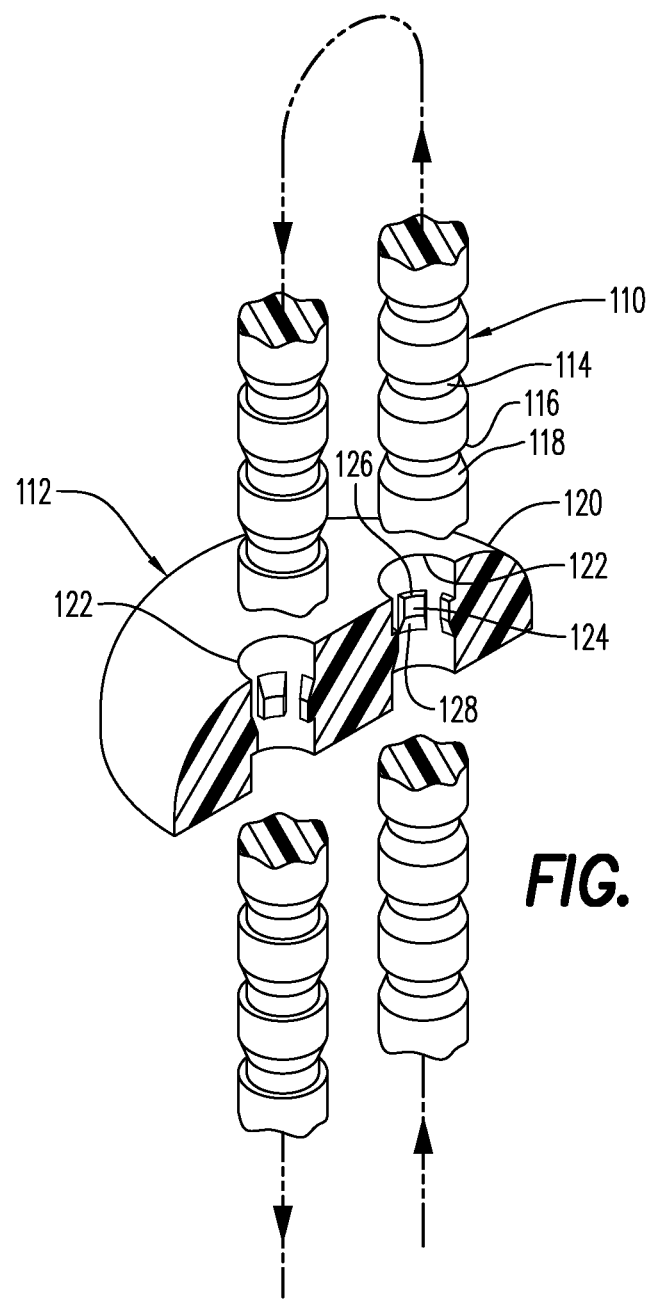

FIG. 34 is a broken perspective view of another embodiment of a suture operatively engaged with cooperatively structured suture tissue restraint.

Exemplary embodiments are illustrated in reference figures of the drawings. It is intended that the embodiments and figures disclosed herein are to be considered to be illustrative rather than limiting.

DETAILED DESCRIPTION OF THE INVENTION

Figure 1:
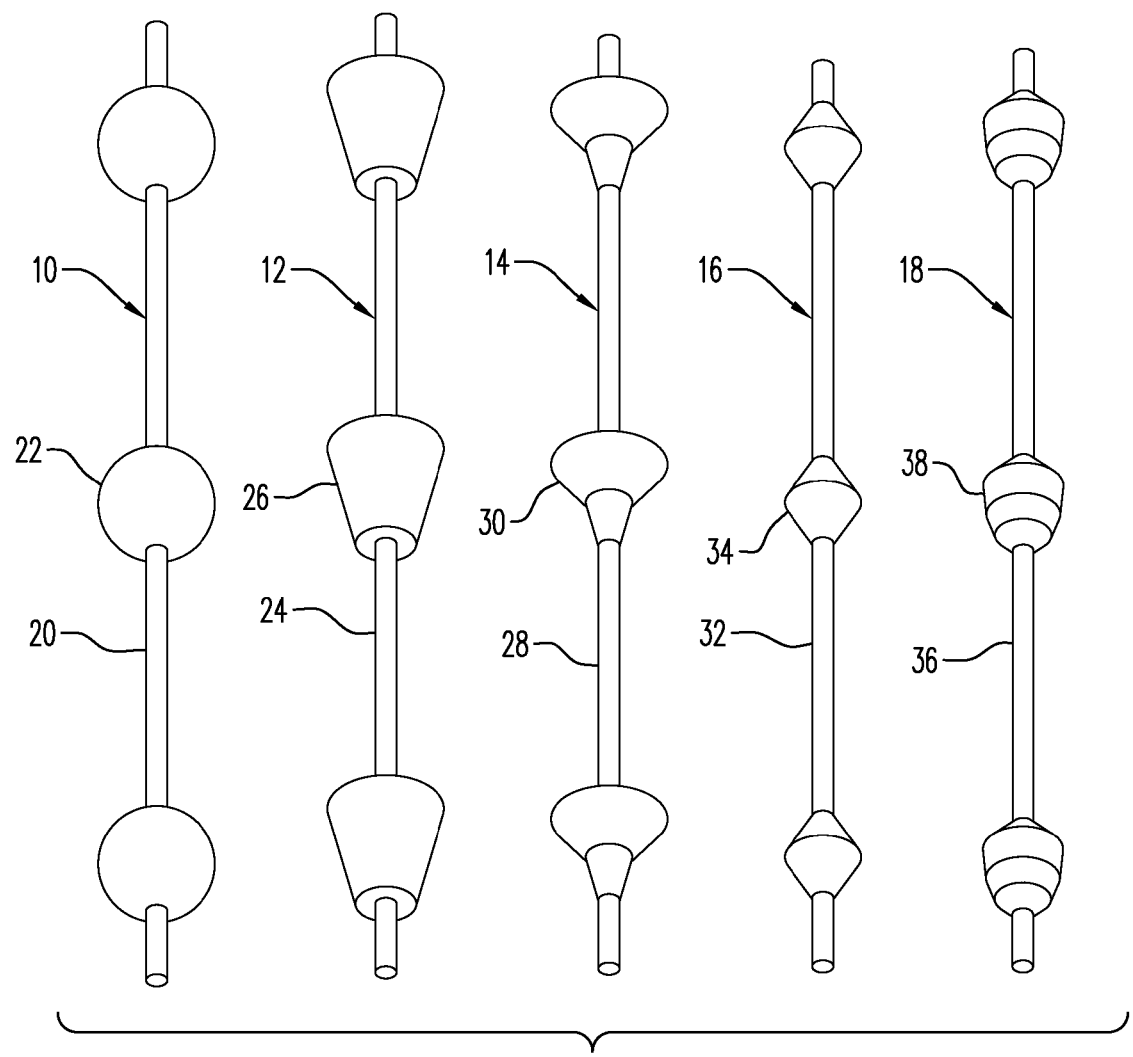
FIG. 1 is a perspective of a plurality of exemplary configurations of sutures each having spaced apart locking protuberances.

Nomenclature 10. suture
12. suture
14. suture
16. suture
18. suture
20. suture strand
22. bead-shaped protuberance
24. suture strand
26. truncated conical protuberance
28. suture strand
30. two-step conical protuberance
32. suture strand
34. symmetric conical protuberance
36. suture strand
38. segmented bullet-shaped protuberance
40. tissue anchor
41. tissue anchor
42. conical anchor body
43. tissue anchor
44. conical anchor body
45. suture entry cavity
46. suture engagement bar
47. suture exit cavity
48. suture locking aperture
49. suture one-way restriction
50. anchor post
51. suture anchor
52. anchor post cavity
53. suture entry aperture
54. tissue anchor top surface
55. suture exit aperture
56. suture tissue restraint
57. suture transverse passage
58. suture locking aperture
59. tissue gripping member
60. suture one-way lock
61. tissue anchor
62. tissue contact surface
63. tissue engaging member
64. suture severance point
65. suture locking aperture
66. suture tissue restraint
67. suture tissue restraint
68. suture locking aperture
69. aperture bevel
70. suture engagement bar
71. suture clearance aperture
72. tissue contact surface
74. open outer surface
76. tissue gripping member
78. suture clearance aperture
80. suture
82. suture strand
84. suture bare strand segment
86. hip prosthesis
88. suture locking aperture
96. orthopedic plate
98. anchor screw holes
100. suture locking aperture
102. tissue gripping member
104. suture clearance aperture
106. suture loop lock
108. suture locking aperture
110. grooved suture
112. suture tissue restraint
114. locking groove
116. groove locking edge
118. groove ramped edge
120. body 122. suture locking aperture
124. locking protuberance
126. locking edge
128. ramped edge Referring now to the drawings, and firstly to FIG. 1, a number of exemplary elongated flexible sutures shown generally at numerals 10, 12, 14, 16 and 18. These sutures are preferably formed of flexible or semi-flexible medically implantable material. Each of these sutures include longitudinally spaced, enlarged-in-diameter segments or protuberances 22, 26, 30, 34 and 38 formed along the length of the corresponding slender suture strand 20, 24, 26, 38 and 36.

Suture 10 is formed having protrusions 22 which are substantially spherical or bead-shaped. Suture 12 includes the protuberances 26 which are in the form of a truncated cone, while suture 14 includes protuberances having a two-step truncated conical structure. Suture 16 includes protuberances 34 having opposing truncated conical portions forming each of the protuberances, while suture 18 has a gradual three step enlargement to each of the protuberances, ending in a sharply truncated conical end or tail portion thereof to interact with suture locking apertures described below.

Figure 2:
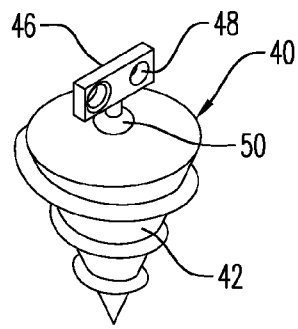
FIG. 2 is a perspective view of a suture anchor configured in accordance with this disclosure.
Figure 3:
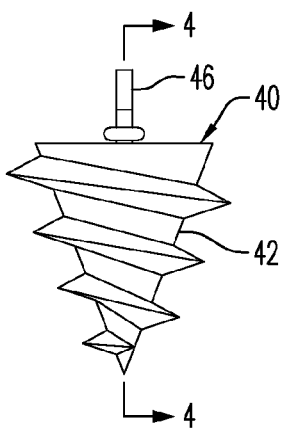
FIG. 3 is a side elevation view of FIG. 2.
Figure 4:
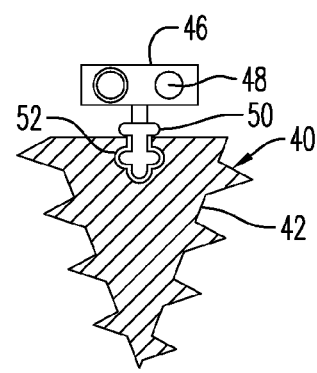
FIG. 4 is a section view in the direction of arrows 4-4 in FIG. 3.

Referring now to FIGS. 2 to 4, one embodiment of a tissue anchor within the scope of this invention is there shown generally at numeral 40 and is formed of a medically implantable material. This tissue anchor 40 includes a conical anchor body 42 having outwardly extending spiral threads which tightly lockingly engage into a tissue substrate such as bone or cartilage. As with all of the tissue anchors and suture tissue restraints disclosed within the scope of this invention, this tissue anchor 40 includes a suture engagement bar 46 having a pair of closely spaced apart suture locking apertures 48 which are sized in diameter and having one end thereof beveled so that, as will be described in detail herebelow, restrict an appropriately configured suture as described in FIG. 1 hereinabove to pass snugly through each of the suture locking apertures 48 in only direction. That is to say that the suture may be drawn into each of the suture locking apertures 48 and pulled therethrough in one direction, but reversal of movement of the suture within these suture locking apertures 48 is prohibited or substantially inhibited so as to effect a locking position in one-way movement fashion of the suture therethrough.

The suture engagement bar 46 includes an anchor post 50 which snappingly and lockingly engages into a mating anchor post cavity 52 formed into the enlarged head proximal end of the anchor body 42 so that the suture engagement bar 46 may be rotated about the longitudinal axis of the anchor body 42 relatively freely so as to quickly and easily rotationally orient the suture engagement bar 46 to a neutral tension force applied by the suture when tightened.

Figures 4A, 5:
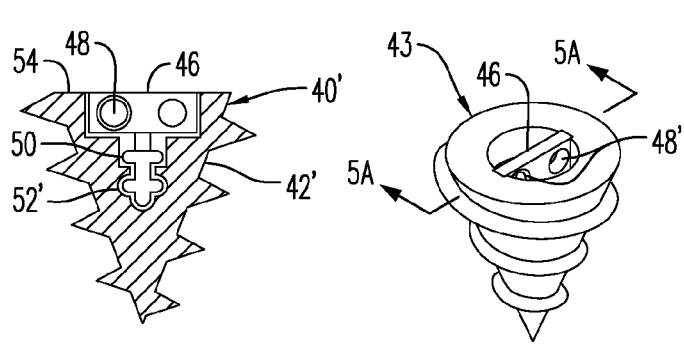
FIG. 4A is a section view similar to FIG. 4 depicting an alternate embodiment thereof.
FIG. 5 is a perspective view of another alternate embodiment of the suture anchor of FIG. 2.

Referring now to FIG. 4A, an alternate embodiment of the tissue anchor 40 is there shown at numeral 40' wherein the entire suture engagement bar 46 is recessed flush with the upper enlarged top surface 54 of the anchor body 42'. Thus, once the suture has been passed through the suture locking apertures 48 after the suture engagement bar has been snappingly engaged into anchor post cavity 52' and the anchor post 50 has been thusly secured therewithin, the top or outer edge of the suture engagement bar 46 is substantially even with the enlarged top surface 54 of the tissue anchor 40'.

Figure 5A:
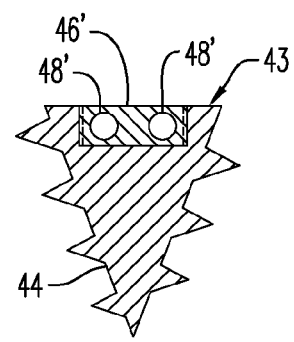
FIG. 5A is a section view in the direction of arrows 5A-5A in FIG. 5.

Referring now to FIGS. 5 and 5A, yet another embodiment of the tissue anchor is there shown generally at numeral 43. This tissue anchor 43 includes a conical anchor body 44 having outwardly extending spiral threads and a fixed transverse suture engagement bar 46' which is secured within a circular cavity formed into the head of the anchor body 44. Again, the suture engagement bar 46' includes two spaced suture locking apertures 48' each having cooperatively oriented bevels so that a selected suture will pass in only direction through the pair of suture locking apertures 48'. This embodiment 43 affords a one-piece structure with the suture engagement bar 46' secured in place and in flush alignment with the head of the anchor body 44 which is the preferred configuration of a tissue anchor of this type.

Although not shown in FIGS. 2 to 5, the head of each of the tissue anchors will be provided with tightening cavities formed into the enlarged end of the anchor body so that a separate tool may be used to drivingly engage the spiral threads into the appropriate bone or cartilage substrate. The tissue anchor 43 in FIGS. 5 and 5A may be rotationally drivingly engaged into the tissue substrate by engagement of an appropriately configured tool onto the suture engagement bar 46' which is rigidly secured in the position shown.

Figure 5B:
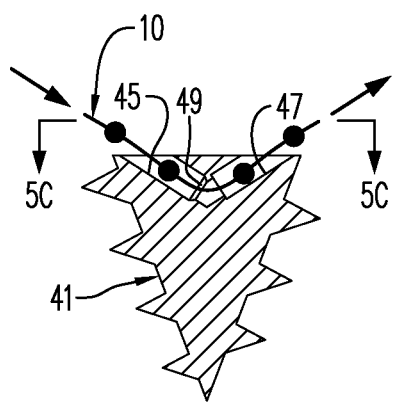
FIG. 5B is a section view of another alternate embodiment of the suture anchor of FIG. 2.
Figure 5C:
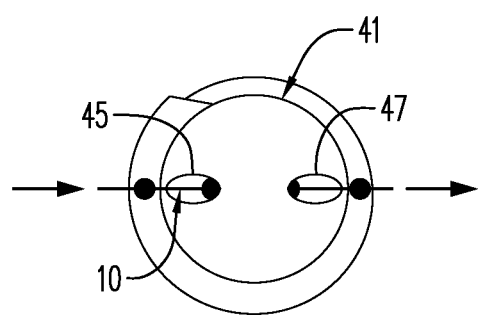
FIG. 5C is a top plan view in the direction of arrows 5C-5C in FIG. 5B.

In FIGS. 5B and C, another configuration of a tissue anchor 41 is there shown configured similarly to the tissue anchors 40, 40' and 43 previously described. However, this tissue anchor 41 includes diagonally oriented intersecting apertures 45 and 47 which converge centrally of the anchor body adjacent to the enlarged head thereof and are sized to receive and permit only one-way movement of the suture 10 in the direction of the arrows. A one-way restriction 49 is provided so as to insure that, once tightened by pulling in the direction of the arrows, the suture 10 may not be moved in the opposite direction.

Figure 5D:
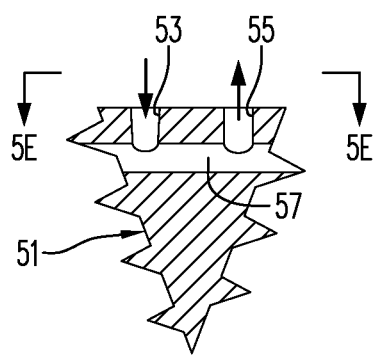
FIG. 5D is yet another alternate embodiment of the suture anchor of FIG. 2.
Figure 5E:
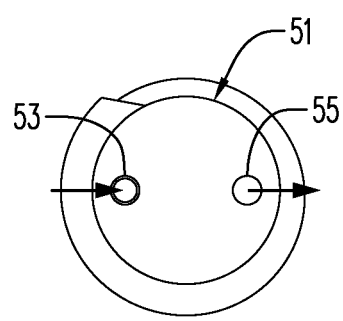
FIG. 5E is top plan view in the direction of arrows 5E-5E in FIG. 5D.

In FIGS. 5D and E, yet another tissue anchor is there shown generally at numeral 51 which also includes a pair of spaced parallel suture entry and exit apertures 53 and 55 which are interconnected by a transverse passage 57. The suture entry aperture 53 is beveled and tapered so as to facilitate only one-way movement of the suture therethrough and exiting from the suture exit aperture 55 only in the direction of the arrows shown.

Figure 6:
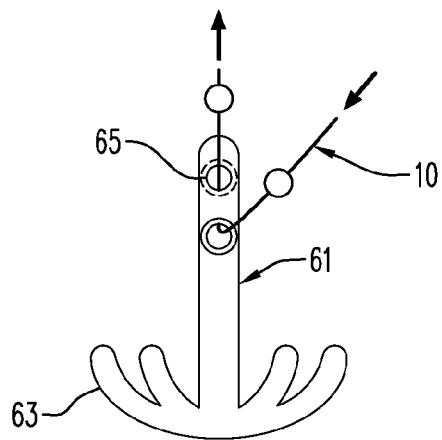
FIG. 6 is a side elevation view of another embodiment of a suture anchor of this disclosure.

Referring now to FIG. 6, another tissue anchor is there shown generally at numeral 61 formed of a medically suitable material having an elongated shank having two closely spaced apart suture locking apertures 65 and 67 formed therethrough and a plurality of circumferentially spaced radially extending tissue engaging members 63. The locking apertures 65 include oppositely oriented bevels so that the suture may be drawn through the pair of locking apertures 65 in only the direction of the arrows.

Figure 7:
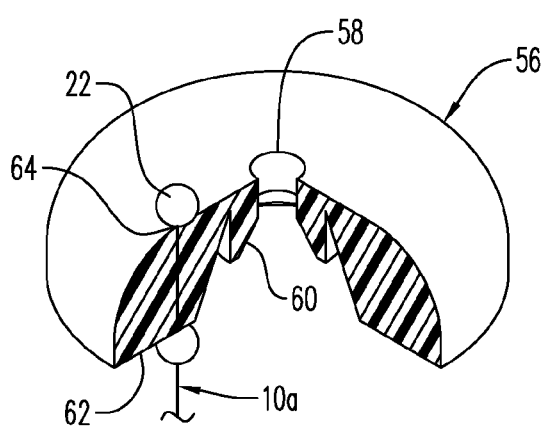
FIG. 7 is a broken perspective view of one embodiment of a suture tissue restraint.

Referring now to FIG. 7, one embodiment of a suture tissue restraint is there shown generally at numeral 56. This tissue restraint 56 may be formed of medically acceptable material. The body is domed-shaped having a flat tissue contact surface 62 and a central suture locking aperture 58 having a one-way suture lock 60 formed around the suture locking aperture 58 which prevents the suture from being drawn downwardly once a suture has been appropriately tensioned upwardly through the locking aperture 58. A second suture 10a is permanently connected through the body of the suture tissue restraint 56 extending downwardly from the flat tissue contact surface 62. However, the suture 10a may be cut at 64 and removed where a repair of tissue procedure only requires a single suture to be lockingly engaged within the suture locking aperture 58.

Figure 7A:
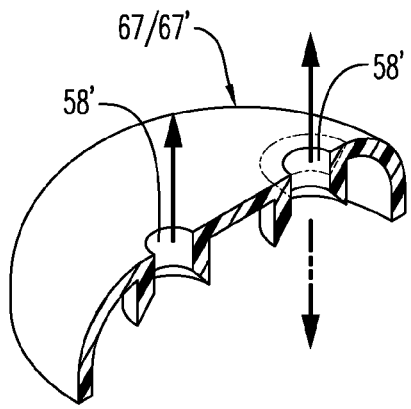
FIG. 7A is a broken perspective view of another embodiment of a suture tissue restraint.

In FIG. 7A, another suture tissue restraint is there shown generally at numeral 67 or 67' and formed having a domed-shaped body similar to that shown in FIG. 7. However, in this embodiment 67/67', two spaced apart suture locking apertures 58' are formed through the dome portion of the tissue restraint 67/67' in closely spaced relationship facing the tissue engaging side of this tissue restraint 67 so that a suture may be tensioned upwardly or away from the tissue contact surface. However, the bevels of the suture locking apertures 58' may be oriented oppositely one another to form suture tissue restraint 67' to lockingly engage a single suture for one directional movement only. Note that, if formed as shown without the missing portions, these suture tissue restraints may be snappingly engaged over a suture and they continue to function as above described.

Note that hereinbelow, tissue anchors and suture tissue restraints are sometimes collectively referred to as "tissue engaging members".

Figure 8:
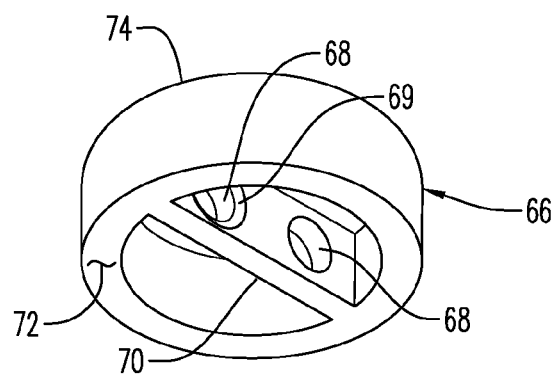
FIG. 8 is a broken perspective view of yet another embodiment of a tissue suture restraint.

Referring now to FIG. 8, another suture tissue restraint is there shown generally at numeral 66 having a ring-shaped body with a flat tissue contact surface 72 and an open outer surface 74. A transversely oriented suture engagement bar 70 formed as a unit with the ring-shaped body is also provided. Two spaced apart suture locking apertures 68 are oppositely beveled at 69 so as to provide the one-way locking engagement of a suture passing therethrough as previously described.

Figure 9:
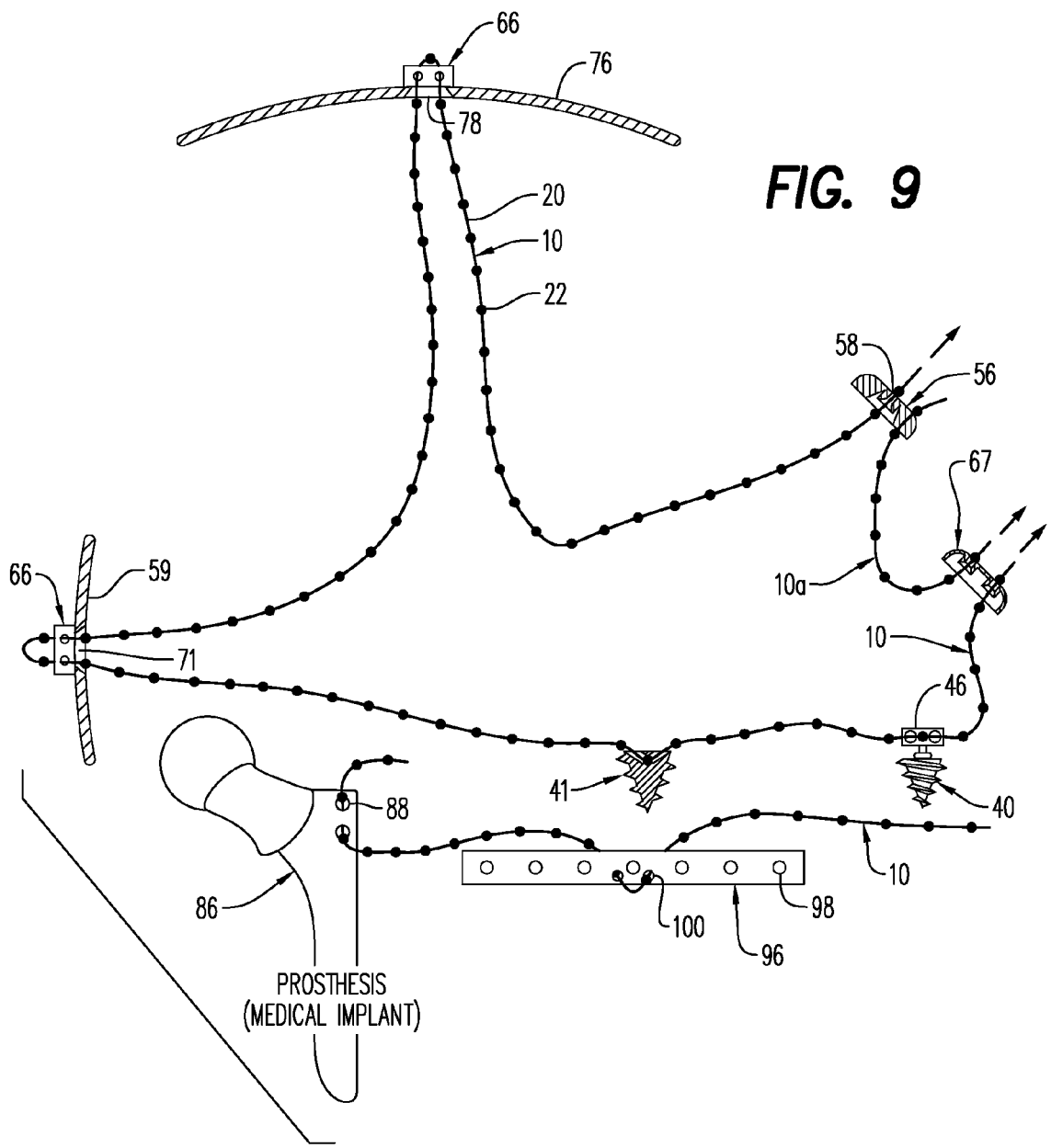
FIG. 9 is a pictorial view showing a variety of suture anchors and suture tissue restraints (absent tissue or tissue substrate for clarity) in locking engagement with one embodiment of the suture member 10 shown in FIG. 1.

Referring now to FIG. 9, a pictorial view showing a variety of tissue engaging members in relation to sutures 10 and 10*a* are there shown. The suture 10 is lockably engaged through the two spaced locking apertures of the suture tissue restraint 66 when positioned against a flexible tissue gripping member 59 which provides a larger tissue contact surface which will biasingly flex against the tissue or tissue substrate to maintain tension produced by the suture when suitably positioned through a suture clearance aperture 71 formed centrally through the tissue gripping member 59. Suture 10 is also shown passing through another suture clearance aperture 78 formed centrally through an enlarged tissue gripping member 76 and in one-way locking engagement with another suture tissue restraint 66.

The suture 10 also extends through the suture locking aperture of the suture tissue restraint 56 for tensioning of the suture in the direction of the arrow. The suture 10*a* which is permanently engaged at one end thereof into the body of the suture tissue restraint 56 as previously described then extends to one of the locking apertures of suture tissue restraint 67 while another portion suture 10 extends from the other locking aperture of the suture tissue restraint 67 for engagement through the dual locking apertures of the suture engagement bar 46 of the tissue anchor 40. This portion of suture 10 is then shown continuing on for locking engagement through suture entry and exit cavities 45 and 47 of tissue anchor 41 and then returning to the suture tissue restraint 66 through suture clearance aperture 71.

Still referring to FIG. 9, another suture 10 may also be lockingly passed through spaced locking apertures 100 formed through an elongated orthopedic plate 96 which is also provided with spaced anchor screw holes 98. Again, the spaced locking apertures 100 are cooperatively arranged and configured to allow for movement of the suture 10 in only direction therethrough. This suture 10 is shown continuing on to be lockingly engaged for one directional movement only through suture locking apertures 88 formed through a suitable portion of a typical hip prosthesis 86 or other medical implant, knee prosthesis, breast implant, cardiac pacemakers as examples but not to represent an all inclusive list, to which the suture 10 may be suitably anchored and tensioned as previously described.

Referring now to FIG. 10, another exemplary installation arrangement utilizing the elongated suture 10 is there shown. In this embodiment, the suture 10 is passed at each end thereof through the spaced locking apertures 68 of the suture tissue restraint 66 which is positioned against a flat enlarged tissue gripping member 102 formed of thin surgical steel or other suitable material and having a suture clearance aperture 104 formed therethrough positionable in alignment with the locking apertures 68 of the suture tissue restraint 66. A mid portion of the suture 10 is lockingly engaged for one directional movement only through the suture engagement bar 46 of the tissue anchor 40 as previously described.

In FIG. 11, a pictorial view of another aspect of the invention utilized to repair and restrain a broken distal phalanx of a finger metacarpal is there depicted. The suture 10 is lockingly passed through passageways drilled or formed through the broken bone ends, a mid portion of the suture 10 passing lockingly through the spaced locking apertures of the suture tissue restraint 66, each end of the suture 10 then lockingly passed through the suture tissue restraint 67 and tensioned in the direction of the arrows to secure the fracture for healing.

In FIG. 12, repair of a torn ACL tissue of a knee joint is there depicted. The suture 10 is passed through passageways formed in the femur and the tibia in aligned opposing fashion, a mid portion of the suture passing through the spaced locking apertures of the suture tissue restraint 66 and the free ends of the suture 10 lockingly engaged through the locking apertures formed through the suture tissue restraint 67.

In FIG. 13, a torn MCL of a knee joint is shown being repaired wherein a modified suture 80 having no protuberances along one end 84 thereof is shown surgically attached to the torn end of the MCL, the suture 80 then passing through spaced locking apertures of the suture engagement bar 46 of the tissue anchor 40 which has been previously secured into the lower end of the femur.

In FIG. 14, the repair of a torn medial patella-femoral ligament is there shown wherein one end 84 of a the suture 80 not having protuberances is surgically attached to the torn distal end of the ligament, the suture 80 then extending to the pair of locking apertures formed through the suture engagement bar 46 of tissue anchor 40 as previously described. The suture 80 then extends to the distal tip of the torn ligament passing therethrough and being secured in position by a suture tissue restraint 56', for added reattaching strength. The suture tissue restraint 56' is as previously described in FIG. 7 wherein the proximal protuberance 22 of suture 10*a* has been cleavered or cut at 64 and removed as being unnecessary.

The repair of a tear in a labrum surrounding a hip socket is shown in FIG. 15. The suture 10 is passed through the locking apertures of the suture engagement bar 46 of tissue anchor 40 which has previously been secured into the hip socket. The suture 10 is then passed through the tear and through the locking apertures of the surgical tissue restraint 67 and tensioned in the direction of the arrows to tighten and repair the tear.

In FIG. 16, the repair of a distal biceps which has become detached is there shown. A modified suture 80 which is absent protuberances at one end thereof at 84 is surgically attached to the distal end of the biceps and then passed through a passageway drilled through the radius and then lockingly engaged through the locking apertures formed through the suture tissue restraint 67'. The free end of the suture 80 may be then passed back through the passageway and through the distal biceps and tensioned in the direction of the arrow to re-secure the biceps for healing.

Reattachment of the fibula in an ankle syndesmodic disruption is shown in FIG. 17. The suture 10 is passed through a drilled transverse passageway adjacent the end of the tibia. A mid portion of the suture 10 is lockingly engaged through the locking apertures of the suture tissue restraint 66 pressed against the tibia. Another suture tissue restraint 67 then receives both ends of the suture 10 after being passed through the lower end of the fibula and tensioned in the direction of the arrows to secure the repair.

Reattachment of the proximal biceps tendon is shown in FIG. 18 wherein a modified suture 80 absent protuberances along a mid portion thereof is wrapped around the proximal biceps tendon and there secured. The protuberance-carrying ends of the suture 80 are passed through the locking passageways of two spaced apart tissue anchors 41, each of which have been previously surgically anchored into the humeral head. The ends of the suture 80 are then tensioned in the direction of the arrows to secure the repair.

In FIGS. 19 and 20, a disc-shaped suture loop lock 106 is provided with spaced apart locking apertures 108 to secure the crisscrossed ends of each suture 10 which is initially passed around the tear formed through the capsule around a shoulder socket. This repair is notably accomplished without the typical tissue anchors, relying upon the tension locking features of each of the suture loop locks 106 as shown in FIG. 20.

FIGS. 21, 22 and 23 show alternate repair techniques utilizing the invention to repair a tear in the shoulder labrum. FIG. 21 provides a total of three separate segments of suture 10 passing therethrough while in FIG. 22, only two separate lengths of sutures 10 are provided. However, in FIG. 23 a total of four segments of two sutures 10 more tightly draw the tear together for repair.

Repair of a detached coracoclavicular ligament is shown in FIG. 24 which utilizes two separate sutures 10 each passing through drilled passageways formed through the clavicle and the coracoid as shown. The ends of each of the suture 10 are secured through modified suture tissue restraints 56' as previously described. Tensioning of all four ends of the sutures 10 provide for both strength and refined tension adjustment of the repair.

In FIGS. 25 and 26, the repair of a subscapularis detachment is there shown wherein two sutures 10 each pass through a passageway formed through the humeral head with modified suture tissue restraints 56' restraining each end of each of the sutures 10 as previously described.

The attachment of a torn rotator cuff tendon is shown in FIG. 27 utilizing a single suture row technique. The suture 10 is passed at each end thereof through the locking apertures of each tissue anchor 40 which have been previously secured into the ends of the humerus. The suture 10 is then previously passed through the rotator cuff tendon and tensioned at each end thereof in the direction of the arrows. In FIGS. 28 and 29, a double row repair of the rotator cuff tendon is there shown where two parallel sutures 10 are each passed through tissue anchors 40 and through the rotator cuff tendon as shown. In FIG. 29, an additional locking and retaining function against the rotator cuff tendon is provided by a modified suture tissue restraint 56'.

Meniscus repair is demonstrated by the use of the invention in FIGS. 30 and 31. In FIG. 30, the meniscal tear is longer requiring a total of four suture segments therethrough using two separate sutures 10. One of the sutures 10 is passed three times through the tear and anchored at a mid-portion thereof through suture tissue restraint 66 and permanently at one end thereof within suture tissue restraint 56. The permanently secured suture 10 of the suture tissue restraint 56 is then passed through the repair, exiting the opposite surface of the meniscus as shown.

In FIGS. 32 and 33, an alternate technique for meniscal tear repair is there shown wherein, in FIG. 32, a single suture 10 is passed three times through the tear utilizing the suture tissue restraints 66 and 56' as shown. In FIG. 33, a total of four passes through the tear is provided wherein the free ends of the suture 10 are drawn from the torn meniscus without the need for suture restraint.

Referring now to FIG. 34, reversal of locking protuberances and apertures is there demonstrated to be within the broad scope of this invention. Flexible elongated suture 110 is shown lockingly engaged for one-directional movement only within a pair of closely spaced locking apertures 122 of a suture tissue restraint 112. The suture has a series of spaced locking grooves formed therein which have a locking edge 116 and a ramped edge 118. Each of these grooves 114 are matingly engageable with radially inwardly extending protuberances 124 each having a square locking edge 126 and a ramped edge 128 to accomplish unidirectional movement of the suture 110.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, the surgical tissue engaging member comprising:
   a body including two spaced apart locking apertures extending diagonally from an outer surface of said body to converge and intersect within an interior of said body defining a passage between said locking apertures; and
   a one-way restriction disposed in said passage in said body member, said restriction being sized to receive said suture member passing therethrough to cooperatively restrict, longitudinal movement of said suture member to only one direction through said locking apertures and said passage.

2. The surgical tissue engaging member as set forth in claim 1, wherein said surgical tissue engaging member is formed as a tapering shape threaded tissue anchor having said spaced apart locking apertures formed through a head thereof.

3. The surgical tissue engaging member as set forth in claim 1, wherein said two spaced apart locking apertures position one protuberance at a different distance from a tissue contact surface of said body.

4. The surgical tissue engaging member as set forth in claim 1, wherein each of said two spaced apart locking apertures extends substantially linearly along, the length thereof from said outer surface of said body to said interior of said body.

5. A surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, the surgical tissue engaging member comprising:
   a body including an entrance locking aperture and an exit locking aperture;
   said entrance locking aperture and said exit locking aperture being spaced apart and converging from an outer surface of said body to intersect within an interior of said body;

said intersection of said entrance locking aperture and said exit locking aperture defining a passage in said body member between said entrance locking aperture and said exit locking aperture;
a one-way restriction disposed in said passage proximate said intersection of said entrance locking aperture and said exit locking aperture;
a one-way restriction enabling said suture member to pass through said entrance and exit locking apertures in a first direction from said entrance locking aperture to said exit locking aperture; and
said oneway restriction inhibiting said suture member from passing through said entrance and exit locking apertures in a second direction from said exit locking aperture to said entrance locking aperture for securing said surgical engaging member to said body.

6. A surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, the surgical tissue engaging member comprising:

a body including two spaced apart locking apertures converging from an outer surface of said body;
each of said two spaced apart locking apertures extending substantially linearly along the length thereof to intersect within an interior of said body;
said intersection of said entrance locking aperture and said exit locking aperture defining an passage in said body member between said entrance locking aperture and said exit locking aperture;
a one-way restriction disposed in said passage proximate said intersection of said spaced apart locking apertures being sized to receive and pass therethrough said plurality of longitudinally spaced protuberances of said suture member through said locking apertures in a first direction; and
said one-way restriction being configured to cooperate with said plurality of longitudinally spaced protuberances of said suture member to restrict longitudinal movement of said suture member from said locking apertures in a second direction.

* * * * *